United States Patent [19]

Roggenkamp

[11] 4,448,307
[45] May 15, 1984

[54] DENTAL SUPPLY DISPENSER

[76] Inventor: Clyde L. Roggenkamp, 1152 N. White River Pkwy. #512, Indianapolis, Ind. 46222

[21] Appl. No.: 386,449

[22] Filed: Jun. 9, 1982

[51] Int. Cl.$^3$ .................. B65D 1/24; B65D 1/36; B65D 85/20
[52] U.S. Cl. .................... 206/369; 206/362; 206/370; 206/379; 220/20; 312/209
[58] Field of Search ............. 206/224, 363, 364, 368, 206/369, 370, 379, 570, 581, 803, 823, 362, 214; 220/20, 20.5, 21, 22; 312/138 R, 140.4, 198, 206, 207, 209, 244, 232; 433/77, 79

[56] References Cited

U.S. PATENT DOCUMENTS

| 727,166 | 5/1903 | Harrison et al. | 312/209 |
|---|---|---|---|
| 910,041 | 1/1909 | Campbell | 312/232 |
| 2,014,516 | 9/1935 | Beddingfield | 312/138 |
| 2,386,573 | 10/1945 | Randall | 220/22 |
| 2,971,637 | 2/1961 | Simons | 206/369 |
| 3,506,324 | 4/1970 | Fristedt | 206/224 |
| 3,817,588 | 6/1974 | Helmers | 312/209 |
| 4,139,096 | 2/1979 | Sieger | 220/20 |
| 4,266,835 | 5/1981 | Schmidt | 312/244 |
| 4,384,647 | 5/1983 | Schweizer | 206/214 |
| 4,406,368 | 9/1983 | Hermes | 206/214 |

FOREIGN PATENT DOCUMENTS 860150  9/1940  France ............... 312/DIG. 33

Primary Examiner—George E. Lowrance
Assistant Examiner—Jimmy G. Foster
Attorney, Agent, or Firm—LeBlanc, Nolan, Shur & Nies

[57] ABSTRACT

A portable dispenser and container apparatus for dental supplies and tools is disclosed. The apparatus includes an elongated multicompartmented container having spaced transverse partitions which define a plurality of frontally open compartments for dental supplies and instruments. A horizontal top wall for the interior group of compartments is provided with a multiplicity of openings of various diameters for receiving the shanks of dental burs or other rod-like dental instruments. The end compartments are open at the top to provide easy access to various longer instruments and supplies as well as jars of dental treatment liquids. A hinged door is mounted over the opening to one of the compartments, the door serving to house a dental supply dispenser such as a cotton pellet dispenser. The apparatus may be semipermanently mounted on a dental office tray if desired. The present apparatus provides quick and convenient access to a wide variety of dental instruments and equipment.

12 Claims, 5 Drawing Figures

U.S. Patent May 15, 1984 Sheet 1 of 2 4,448,307
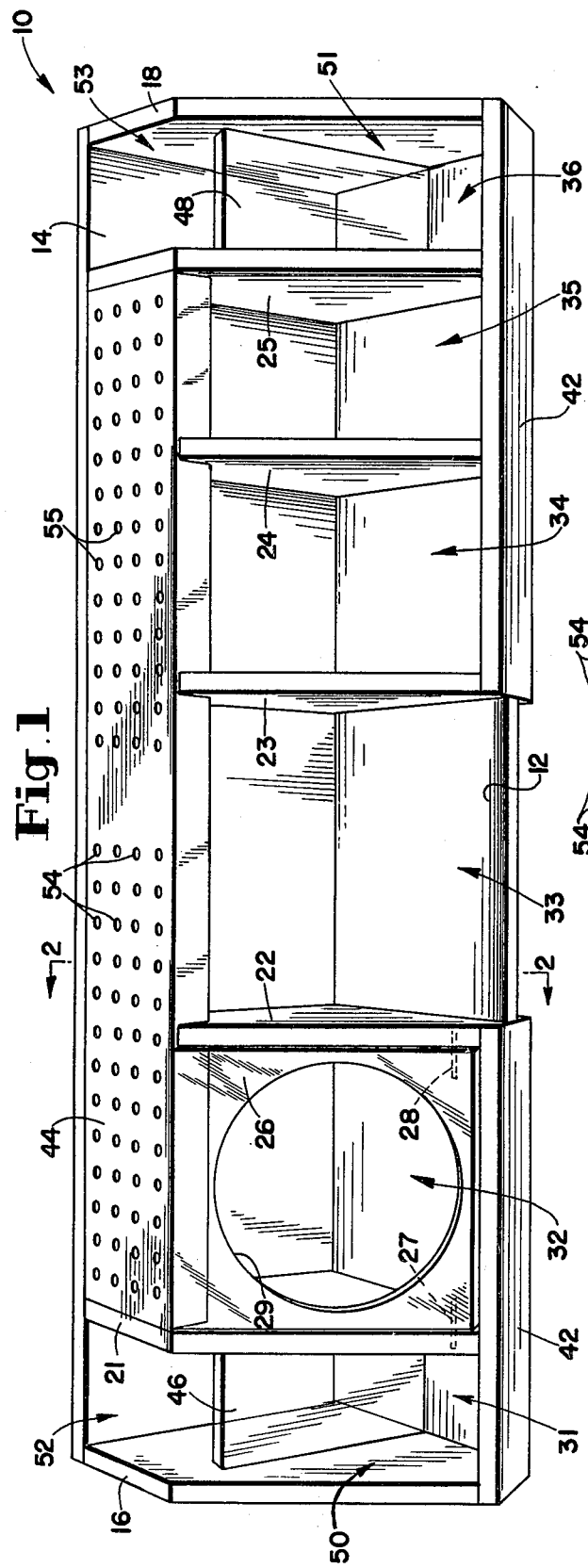
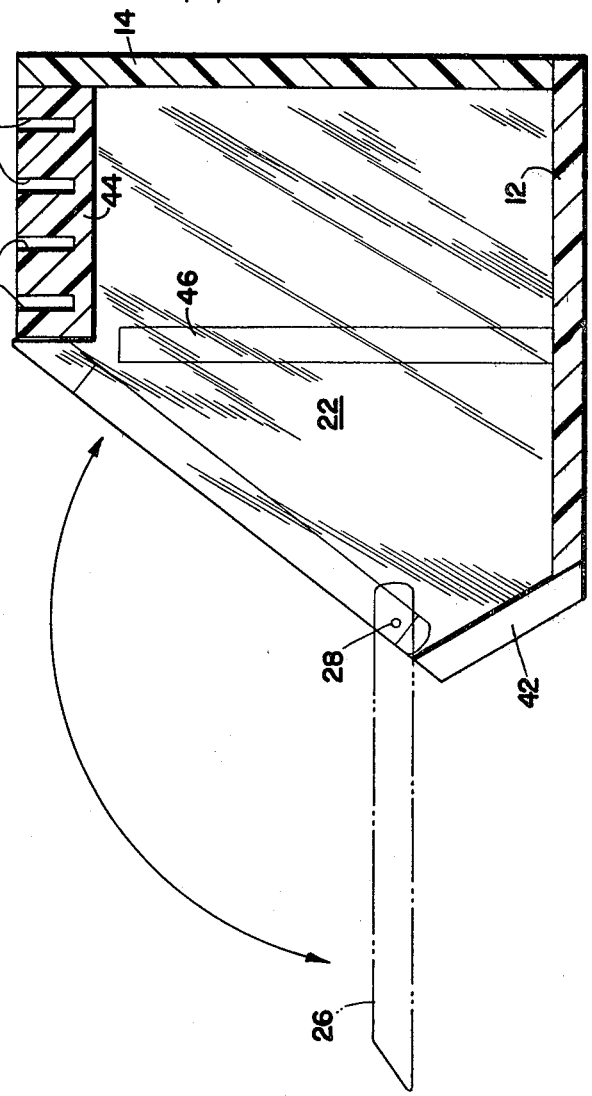

DENTAL SUPPLY DISPENSER

BACKGROUND AND SUMMARY OF THE INVENTION

The present invention relates to a dispenser and container for dental supplies and equipment. More particularly, the present invention relates to a portable dispenser or holder which provides for convenient storage and utilization of instruments and supplies used by a dentist.

In carrying out the various dental drilling and treatment procedures associated with the practice of dentistry, the dentist requires immediate access to an assortment of dental instruments and supplies. The consolidation of frequently used dental instruments, supplies and the like in an easily accessible arrangement which takes into account such factors as size, weight and frequency of use of the individual items would be of great benefit to the practicing dentist.

In some situations, for example, it is necessary for the dentist to change the bur in the drill or to reach for a dental supply item with one hand while the other hand is positioned in proximity to the mouth of the patient. Also it is frequently necessary for the dentist to perform treatment upon several patients practically simultaneously, with such patients being located in adjacent rooms of the dental office. In other situations, the dentist is required to transport his equipment to treatment areas outside the office such as, for example, when treating patients in a hospital or rest home or in the case of an emergency. In carrying out any of these various dental practices and treatments, it would be highly advantageous for the dentist to have at hand a lightweight, portable container or carrier which would provide convenient and quick access to many of the often used dental supply items and instruments employed during treatment.

Various containers and holders for dental instruments and supplies are described in the prior art, including the following U.S. Pat. Nos.: 4,191,291 to Brown; 1,519,614 to Heck; 3,102,637 to Scholl; 3,270,416 to Massa; 4,256,457 to Behring; and 4,293,074 to Dunsky.

The Brown patent discloses a dental organizer and container device having a relatively large flat upper surface which supports a removable rectangular tray, the device further including a plurality of posts which support various dental clamps and a plurality of holes for receiving various files, burs and the like. The Heck, Scholl and Massa patents describe various dispensers and holders for dental burs, being exclusively directed to such use. The Behring and Dunsky patents relate to various containers or kits for holding dental equipment specifically for use in root canal treatment. None of these patents discloses a dental supply container and dispenser as provided by the present invention, in which a plurality of compartments and storage areas are conveniently located at the forward portion of the device for easy access by the dentist.

An object of the present invention is to provide a dental supply unit formed with recesses or compartments which are shaped and located so as to receive specific dental instruments and materials in a predetermined arrangement, with such instruments and materials being located in the same position each time, based upon the size, weight and frequency of use of the items, as well as the sequential order of use thereof, so that with minimal familiarization the dentist can obtain a particular instrument or item by reaching immediately to the same place each time.

A further object of the invention is to provide a dental supply dispenser which is highly portable so as to be easily transported from one location to another.

An additional object of the invention is to provide a dental supply unit which may be easily constructed of relatively inexpensive, lightweight materials, and having a professional appearance in keeping with the environment in which it is used.

A further object of the invention is to provide a dental supply dispenser and container which is large enough to contain a supply of all the instruments and supplies commonly used by a dentist, but which at the same time is sufficiently compact and lightweight so as to be highly portable.

A still further object of the invention is to provide a novel dental supply dispenser which allows the dentist to obtain a instrument or a dental supply item quickly and efficiently.

The foregoing and additional objects and advantages are achieved by the dental supply dispenser of the present invention which is a multicompartmented container having an elongated, reactangular base joined to a similar back, with spaced transverse partitions forming a plurality of frontally open stalls or compartments for dental supplies and instruments. A top plate portion of the dispenser is provided with a plurality of holes for receiving the shanks of dental burs or other rod-like dental tools for ready access. If desired, the dental supply dispenser may be semi-permanently mounted in proximity to the area in which the dental supplies and tools are to be employed. The items which can be accommodated by the present dental supply dispenser include: Various sizes and types of dental burs; cotton tipped applicator sticks; topical anesthetic; cotton rolls and pellets; a dental floss dispenser; gauze; sponges; a vial of dental cavity varnish; and cotton pliers.

BRIEF DESCRIPTION OF THE DRAWINGS

FIG. 1 is a front perspective view of the dental supply dispenser of the present invention.

FIG. 2 is a cross-sectional view taken along line 2—2 of FIG. 1, showing the open and closed positions of a door to one of the compartments of the dispenser.

DESCRIPTION OF THE PREFERRED EMBODIMENTS

Figure 3:
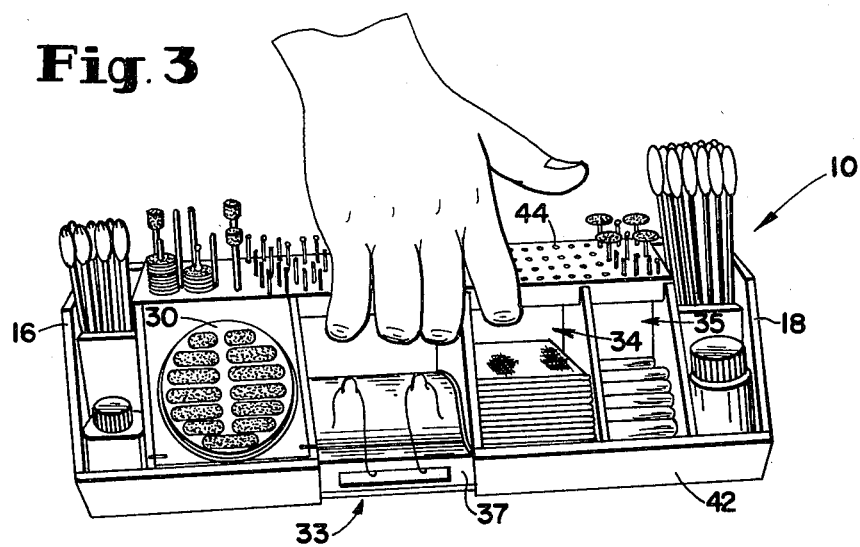
FIG. 3 is a perspective view showing the present dental supply dispenser packed with various dental supply items, and showing a location for the hand of a user when carrying the dispenser from one location to another.

In the embodiments of the present invention as shown in FIGS. 1 through 4, there is provided a dental supply dispenser 10 which includes a planar horizontal base member 12 with vertical back wall 14 and side walls 16, 18 attached by means such as a suitable adhesive and extending vertically upward therefrom. A series of spaced vertical partition walls 21 through 25 are attached to and extend upwardly from the base member 12 in parallel relation to the side walls 16, 18. Each of the side walls 16, 18 and partition walls 21 through 25 is attached to and intersects the back wall 14 at a right angle to define a series of compartments 31 through 36.

Extending at an angle outwardly and upwardly from the front edge of the base member 12 is a short front wall 42. In one embodiment, front wall 42 extends outwardly at an angle of approximately 30 degrees from the vertical. The front wall 42 is attached to and extends along the entire front edge of the base member 12 with the exception of that portion of the base member 12 which defines centrally located compartment 33. Thus compartment 33 is completely open at the front end thereof, allowing compartment 33 to be utilized for larger dental supply items such as a conventional dental floss dispenser 37.

The side walls 16, 18 and partition walls 21 through 25 have parallel front edges which are attached to and abut outwardly extending front wall 42 and then extend upwardly and inwardly in parallel relation from the top of the front wall 42 to points of intersection with the horizontal upper surfaces of the dispenser 10. A horizontal top wall 44 rests in suitable indentations in the upper edge of partition walls 22, 23 and 24. Top wall 44 is attached to and abuts the top portion of partition walls 21, 25 so that the upper surface of top wall 44 is substantially coplanar with the top surfaces of each of the side walls 16, 18 and partition walls 21 through 25.

In the end compartments 31, 36 there are provided respective vertical partitions 46, 48 which are positioned approximately midway between the front 42 and back 14 walls and extend parallel to the back wall 14, being secured between the respective side wall 16, 18 and the adjacent partition wall 21, 25. Partitions 46, 48 are attached to and extend upwardly from the base member 12 approximately three-fourths of the distance from base member 12 to the upper surface of respective side walls 16, 18. Thus there are provided a separate front 50, 51 and rear 52, 53 cubicle for each of the end compartments 31, 36.

The present dental supply dispenser 10 may be constructed of a lightweight durable material such as clear acrylic plastic, of a thickness such as about ¼ inch, except for the top wall 44 which has a thickness of about ½ inch. The dispenser 10 may also be constructed of autoclave resistant materials if desired. In one embodiment, the dimensions of the dispenser 10 include a length of about 15 inches, a depth of about 4 inches and a height of about 3¾ inches.

Located in the top wall 44 are a plurality of openings 54, 55 in the form of holes which may be of various lengths and diameters. In one embodiment, as shown in FIG. 2, the openings 54, 55 have a length which is only slightly less than the thickness of top wall 44. Thus, for example, with a top wall 44 having a thickness of about ½ inch, the openings 54, 55 may be approximately ⅜ inches deep and 1 cm apart, with the openings 54 on the left side of the dispenser 10 having a diameter of about 3/32 inches and the openings 55 on the right side of the dispenser 10 having a diameter of about 1/16 inch, and with a 1 inch space separating the two groups of different sized openings 54, 55. The purpose of the openings 54, 55 is to receive the dental burs 56 and similar rod-like instruments as shown in FIG. 3. It is also within the scope of the invention to provide one large or multiple smaller, removable bur-holding blocks (not shown) instead of said fixed bur-holding arrangement.

Figure 4:
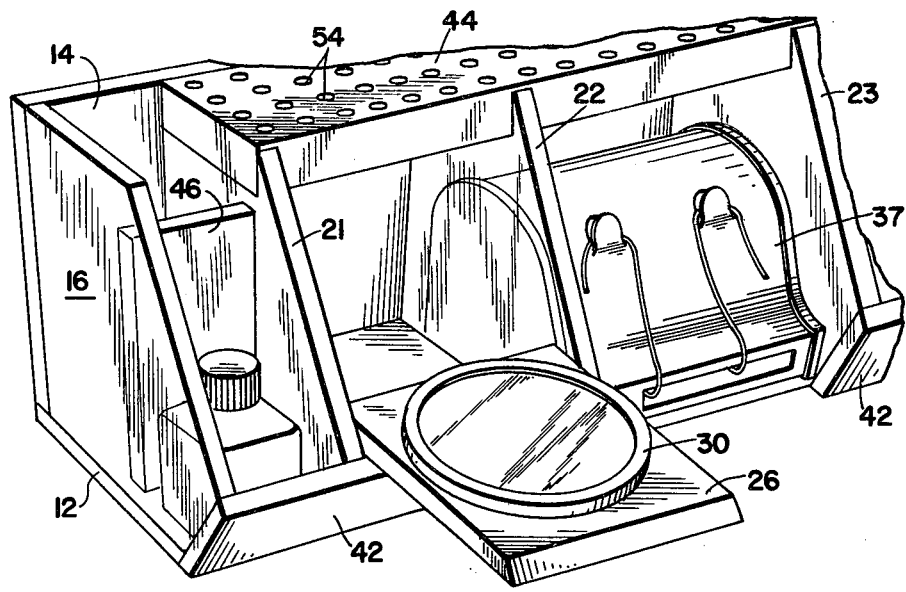
FIG. 4 is a partial perspective view from the left side of the dental supply dispenser of FIG. 1, showing various supply items in position within the dispenser and with a door to one of the compartments shown in the open position.

Compartment 32 is provided with a door 26 which is attached by hinge pins 27, 28 to partition walls 21, 22 and fits between walls 21, 22 so as to be coplanar with the forward surfaces thereof when the door 26 is in the closed position, as shown in FIG. 2. The length of door 26 should be such as to provide for a slight extension beyond the top wall 44 when the door 26 is in the closed position, with the extension serving as a finger grip to allow the door 26 to be readily opened. An opening 29, of a circular or other convenient shape, is provided in the door 26 for receiving a conventional refillable cotton pellet dispenser 30 which is friction fitted therein, as shown in FIGS. 3 and 4. The area within compartment 32 behind the cotton dispenser 30 serves as a useful storage space for any of various items such as emergency ammonia capsules, gingival retraction cord or other items which are used on a less frequent basis or which need not be quite so readily available.

Figure 5:
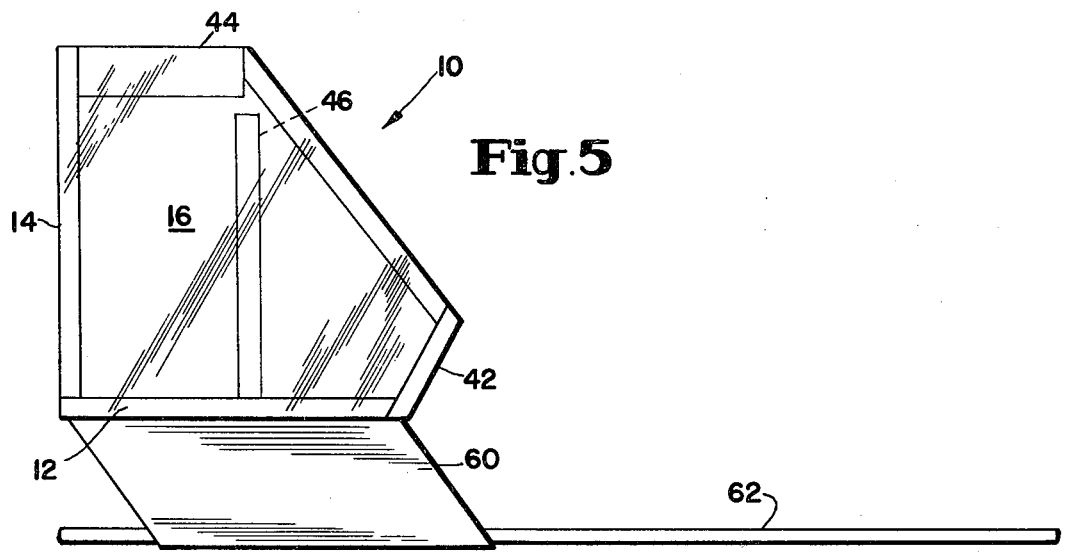
FIG. 5 is a side elevation of the dental supply dispenser of FIG. 1, showing the dispenser mounted on a tray.

In FIG. 5 there is shown an end view of one embodiment of a tray mounting platform 60 which allows the dental supply dispenser 10 of the present invention to be semi-permanently mounted on a horizontal tray 62 located in proximity to the dentist during treatment of patients. The mounting platform 60 may be formed of a suitable material such as sheet metal, for example, which is attached to the tray 62 by conventional means. The dispenser 10, in turn, is attached to the platform 60 by means such as screws or, alternatively, by Velcro fasteners located along the underside of the dispenser 10 which mesh with similar fasteners positioned on the top surface of platform 60. The platform 60 is angled upwardly to the rear, thus allowing the dental supply dispenser 10 to be placed at the rear of the tray area if desired.

With regard to the storage of various small dental instruments and supply items, generally the taller items are located at the rear of the dispenser 10 with the shorter items being carried in the front. Also, the heavier items and tools are generally located in the lower portion of the dispenser 10 adjacent the base 12. As previously discussed, various sizes of dental burs and similar spindle-shaped instruments such as mandrels and vertical shafts for holding stacked abrasive discs are carried in the holes 54, 55 in bur block 44, as shown in FIG. 3. Items to be stored in rear cubicles 52, 53 at the ends of the dispenser 10 include cotton tip applicator sticks, disposable saliva ejector tips and cotton pliers. Items to be stored in the front cubicles 50, 51 would include, for example, jars of topical anesthetic and dental cavity varnish. The forward tilt of front wall 42 provides easy access to such jars which may be angled forward and, in some cases, wedged into the cubicle 50, 51 to assist in allowing the jar to be opened with one hand.

It is pointed out that the contents of the cubicles 50 through 53 at the ends of the dispenser 10 may be interchanged as desired in order to accommodate either a right handed or left handed dentist. In one embodiment, the respective front cubicles 50, 51 are identical in size and shape to enhance this feature of interchangeability of contents between ends of the dispenser 10. Rear cubicles 52, 53 are similarly identical to each other in this embodiment. It is, of course, desirable for a particular jar to be located on the same end of the dispenser 10 as the applicators which are suitable for the contents of the particular jar.

As to the utilization of compartments 32 through 35 located in the interior portion of the dispenser 10, compartments 32 and 33 may, for example, be employed for storage of a cotton pellet dispenser 30 and dental floss dispenser 37 as previously discussed, such items being shown in FIG. 4. Compartment 34 may be employed for storage of gauze sponges, stacked either vertically or end-on, as shown in FIG. 3, with compartment 35 being used for storage of cotton rolls, fitted either sideways or end-on.

In FIG. 3 there are shown the highly portable features of the present dispenser 10 wherein the fingers of the person carrying the dispenser 10 may be tucked under the bur block 44 on the front side of the dispenser 10, with the fingers extending through the open front ends of compartments 33 and 34 located in the central portion of the dispenser 10.

The present invention is constructed so as to function as a dispenser of dental supplies and instruments, being compact in size and highly portable. Thus in a small space the present dispenser 10 will accommodate the following items: over 100 dental burs in special holes across the top of the unit 10; more than a dozen cotton tipped applicator sticks; a vial of topical anesthetic; a miscellaneous compartment; a whole package of cotton rolls; a refillable cotton pellet dispenser; a refillable dental floss dispenser; gauze sponges; a vial of cavity varnish; cotton pliers; and miscellaneous additional dental supply items and tools.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed and desired to be secured by Letters Patent is:

1. A dental supply dispenser and instrument holder apparatus comprising: a planar elongated base member having front and rear side walls, end walls and transverse partition walls extending upwardly therefrom, said partition walls extending transversely to the longitudinal axis of said base member and being generally parallel to said end walls; said front side wall extending outwardly toward the front from the base at an angle relative to the vertical; said rear side wall extending higher than said front side wall, said end walls and partition walls having parallel front edges which abut said outwardly extending front wall and extend upwardly and inwardly from the top of said front wall, said front and rear side walls, together with said end walls and partition walls, defining a plurality of compartments which are open at the upper front portion thereof, at least one of said compartments having a door with hinge means pivotally connecting said door to said apparatus; a planar top wall attached to the upper portions of said partition walls and extending generally horizontally to enclose the top of at least one of said compartments, said top wall having a plurality of openings in the upper surface thereof for receiving dental burs, said apparatus including a compartment at each end thereof which is free of said top wall so as to be easily accessible for storing items of greater length.

2. The dental apparatus of claim 1 wherein the compartment at each end of the apparatus includes a vertical partition located approximately midway between the front and rear side walls and extending parallel to said rear side wall, said partition dividing each end compartment into a pair of cubicles for storage of dental supplies and tools.

3. The dental apparatus of claim 1 wherein said door is provided with an opening therein for receiving a dental supply container.

4. The dental apparatus of claim 3 wherein said opening is configured to receive a cotton pellet dispenser.

5. The dental apparatus of claim 1 wherein storage space is provided inside said door for storage of dental supply items and small instruments.

6. The dental apparatus of claim 1 wherein said front side wall extends outwardly from the base at an angle of approximately 30 degrees from the vertical.

7. The dental apparatus of claim 1 wherein at least one of said compartments is free of said front wall so that said at least one compartment is open at the front end thereof from the base member to the top wall.

8. The dental apparatus of claim 1 wherein said top wall is provided with a plurality of openings having a first diameter and a plurality of openings having a second diameter.

9. The dental apparatus of claim 8 wherein said first diameter is about 3/32 inch and said second diameter is about 1/16 inch.

10. The dental apparatus of claim 1 wherein said apparatus is constructed of acrylic plastic material.

11. The dental apparatus of claim 1, further including a tray member and means for mounting said dental apparatus upon said tray.

12. The dental apparatus of claim 1 wherein the compartments at the ends of the apparatus are identical in size and shape to accommodate either a right handed or left handed dentist.

* * * * *